United States Patent [19]

Sadowski, Janusz W.

[11] Patent Number: 5,322,798

[45] Date of Patent: Jun. 21, 1994

[54] METHOD FOR CARRYING OUT SURFACE PLASMON RESONANCE MEASUREMENT AND SENSOR FOR USE IN THE METHOD

[75] Inventor: Sadowski, Janusz W., Tampere, Finland

[73] Assignee: Valtion teknillinen tutkimuskeskus, Espoo, Finland

[21] Appl. No.: 962,786

[22] PCT Filed: Jul. 4, 1991

[86] PCT No.: PCT/FI91/00210

§ 371 Date: Dec. 31, 1992

§ 102(e) Date: Dec. 31, 1992

[87] PCT Pub. No.: WO92/01217

PCT Pub. Date: Jan. 23, 1992

[30] Foreign Application Priority Data

Jul. 4, 1990 [FI] Finland .................................. 903357

[51] Int. Cl.[5] ...................... G01N 21/55; G01N 21/63
[52] U.S. Cl. ..................................... 436/113; 356/317;
356/318; 356/345; 435/4; 435/291; 422/82.05;
422/88; 422/83; 436/165; 436/121; 436/131;
436/139; 436/144
[58] Field of Search ...................... 356/317, 318, 345;
422/61, 68.1, 82.05, 82.06, 82.09, 83, 88, 91;
436/139–142, 144, 164, 165, 170, 171, 113, 121,
131; 435/4, 291

[56] References Cited

U.S. PATENT DOCUMENTS 4,765,705 8/1988 Seymour et al. ............... 350/96.15
4,844,613 7/1989 Batchelder et al. ............ 356/318
4,889,427 12/1989 Van Veen et al. ............... 356/445

FOREIGN PATENT DOCUMENTS 0257955 3/1988 European Pat. Off. ...... G01N 21/84
0341927 11/1989 European Pat. Off. ...... G01N 21/75
2197065 11/1986 United Kingdom ........ G01N 21/55

OTHER PUBLICATIONS

WO, A1, 90/11510 (Amersham International PLC) 4 Oct. 1990.
WO, A1, 90/11525 (Amersham International PLC) 4 Oct. 1990.

Primary Examiner—James C. Housel
Assistant Examiner—David Redding

[57] ABSTRACT

In a method for carrying out a surface plasmon resonance (SPR) measurement a beam of electromagnetic radiation is directed through a part transparent to it onto a surface of a material layer having been brought on its opposite side in contact with a test material. A change in the intensity of the reflected radiation, caused by the resonance phenomenon, is utilized for analyzing the test material. The material layer is of catalytic material, for example palladium, having a negative real part of the dielectric constant at the used wavelength of the electromagnetic radiation and being capable of catalyzing chemical reactions in which the test material takes part. The measurement is carried out at such a wavelength and angle of incidence of the radiation onto the surface that a change resulting from the material concentration accumulated on the opposite side of the material owing to the catalytic properties is detectable in the intensity of the reflected radiation.

10 Claims, 1 Drawing Sheet

METHOD FOR CARRYING OUT SURFACE PLASMON RESONANCE MEASUREMENT AND SENSOR FOR USE IN THE METHOD

The invention relates to a method utilizing surface plasmon resonance phenomenon for analyzing various substances, as well as to a sensor for carrying out the method.

BACKGROUND OF THE INVENTION

The surface plasmon is a particular kind of electromagnetic wave which propagates along the surface of a metal (H. Raether, "Surface plasmons on smooth and rough surfaces and on gratings", Springer-Verlag, Berlin, 1988). Optical excitation of the surface plasmon can be achieved if a p-polarized, collimated light beam undergoes total reflection on the surface of glass substrate coated with a thin metal film (so-called Kretschmann configuration). The momentum of photons should match the surface plasmons on the opposite surface of the metal film in order to make this possible. This occurs for a given wavelength at a given critical angle of incidence of light. The phenomenon is observed as a sharp minimum in the intensity of the reflected light when the angle of incidence is varied. The angle or wavelength at which this dip occurs depends decisively on the properties of the surface layer on top of the metal film, and therefore the phenomenon can be used to monitor changes on this surface layer caused e.g. by a specific chemical or biological reaction or by the change of concentration of some substance in the immediate vicinity of this surface.

In principle, any material having a negative dielectric function can be used for the excitation of plasmons Most metals fulfill this requirement in the range of visible wavelengths. An ideal material (SPR-material) should have a negative coefficient of the real part of the dielectric constant and as large an absolute value of this coefficient as possible and at the same time as small an absolute value of the coefficient of the imaginary part as possible. In the previous methods utilizing the SPR-phenomenon the choice of metals and their thicknesses has been made usually to satisfy the criterion for the sharpest peak with as total an extinction of the intensity of reflected light as possible. For this reason the metals most used are silver and gold, silver giving the sharpest peaks. Because of the steep curve the sensitivity of the method is good when a constant angle of incidence is used. When the aim is to improve the dynamics of the method, several angles of incidence can be used additionally for carrying out a simultaneous intensity measurement. The method of the above kind is disclosed for example in GB-Patent Application 2,197,065. It is also possible to observe the location of the peak, that is, the measurement gives more data which are independent of each other.

The SPR-material is in addition coated with a specific surface layer having certain affinity towards the test material to attain desired sensitivity. The changes occurring in this layer form the basis for the measurement.

The purpose of the invention is to present an improvement for the above-mentioned methods and to present a method and sensor making it possible to widen the field of use of the SPR-method. When a catalytically active material is used as the material, the catalytic properties and the SPR-properties of the material can be combined in a way that creates new possibilities of analysis.

The method and sensor can also make use of materials having a relatively large optical absorption. This kind of material, even if it creates a broad peak, can be used in SPR-sensors on the prerequisite that the analyses are carried out at an angle of incidence and wavelength that are properly chosen.

BRIEF DESCRIPTION OF THE DRAWINGS

The invention will be described in the following more closely with reference to the accompanying drawings, wherein.

DETAILED DESCRIPTION OF THE INVENTION

Figure 1:
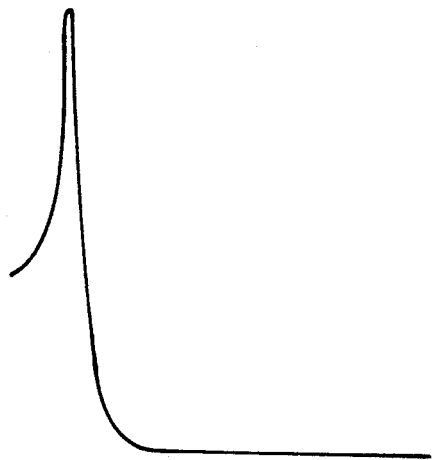
FIG. 1 shows a typical resonance curve obtained using the sensor material of the invention.

The success in a SPR-measurement depends mainly on two factors.

The material of the material layer must be SPR-compatible as such, that is, it must possess some predetermined dielectric properties discussed hereinabove. For ensuring good sensitivity the curve illustrating the intensity as a function of the angle of incidence must have at least one portion that is steep enough so that at this point a small shift of the curve which takes place owing to the changes on the opposite surface of the material layer would cause a change of intensity that is as large as possible.

On the other surface of the material layer the test material must effect a change to cause a sufficiently large change of intensity. This kind of change can be caused by a change in the dielectric properties of the surface resulting from the change of concentration of a substance in the vicinity thereof.

In accordance with the invention, the material layer for the measurement is so chosen that it on one hand is SPR-compatible material as such, and on the other hand its opposite surface facing away from the radiation constitutes an area in which changes in properties influenced by the test material take place owing to the fact that the material layer is of catalytic material being capable to act as a catalyst for some chemical reaction in which the test material takes part. Even if the reaction did not happen on said surface, the catalytic properties of the material towards the test substance will cause the accumulation of the test material on the surface of the material layer in a concentration being sufficiently high to make it possible to detect the change in the SPR-conditions using measurement techniques.

It is clear that on one hand there exist several catalytically active materials, such as metals, that at the same time are SPR-compatible. On the other hand there exist several substances that take part in a reaction that at least one SPR-compatible material is capable of catalyzing in the heterogenous catalysis, in which the catalyst and the reactive material are in different phases. The heterogenous catalyst to be used in the method can be chosen according to the test material and the SPR-compatibility of the catalyst. Examples of some materials commonly used in the heterogenous catalysis and having a negative real part of the dielectric constant are titanium, cobolt, nickel, platinum, aluminum palladium. The properties that have been too poor for traditional SPR-methods (e.g. the lack of a clear peak at the angle of incidence causing a sharp intensity minimum) are no more a bar when said materials will be applied in accordance with the present invention. It must also be noted that even if pure metals are listed above, use can be made also of catalytically active metal alloys and even semiconductors, provided that they have a negative real part of the dielectric constant. The table below lists the dielectric constants of some metals at given wavelengths.

TABLE

Optical constants for some metals

| Metal | wavelength (nm) | dielectric constant | SPR-ratio |
|---|---|---|---|
| Ag | 632.8 | −18.22+i 0.48 | 37.96 |
| Cu | 632.8 | −14.67+i 0.72 | 20.38 |
| Au | 632.8 | −10.92+i 1.49 | 7.33 |
| Al | 650.0 | −42.00+i 16.40 | 2.56 |
| Pd | 620.0 | −14.40+i 14.60 | 0.99 |
| Pt | 640.0 | −11.10+i 15.70 | 0.71 |
| Ni | 620.0 | −9.60+i 14.09 | 0.68 |
| Co | 617.0 | −12.10+i 18.00 | 0.67 |
| Pb | 650.0 | −8.67+i 13.40 | 0.65 |
| Ti | 617.0 | −6.71+i 19.86 | 0.34 |
| Fe | 632.8 | −1.02+i 17.81 | 0.06 |
| Cr | 617.0 | −0.84+i 20.92 | 0.04 |
| V | 617.0 | 3.41+i 21.38 | 0.16 |
| W | 636.0 | 4.30+i 21.32 | 0.12 |

SPR-ratio = the real part of the dielectric constant provided with an opposite sign divided by the coefficient of the imaginary part The wavelength and the angle of incidence of the electromagnetic radiation used in the measurement can be chosen according to the SPR-material and the test material. Light is as a rule mentioned in connection with SPR-methods, but it should be noted that some suitable wavelengths can be situated outside the visible light within the IR-range.

As shown by FIG. 1, for the metals with a relatively large optical absorption the peak of the resonance curve (intensity as function of angle of incidence) is broad and the point of minimum is therefore indefinite. According to the invention the metals having such a broad SPR-response are useful in SPR-measurements if advantage is taken of the catalytic properties of the metals. Consequently, the measurement can always be carried out with a good sensitivity at such an angle of incidence for which the curves illustrating the intensity as a function of the angle of incidence are as distinctly separated from each other as possible in the measurement range for the test material. In this case, for example, the down-way slope of the resonance curve can be used, said slope being effected most by the changes in the resonance conditions. The determination of the shape of the whole curve and the location of the minimum point is not necessary if the measurement is performed within a defined concentration range.

Alternatively, the speed of change of the intensity value can be determined instead of the concentration determinations by means of the absolute intensity values, that is, the time derivative of the intensity starting from the moment when the surface came into contact with the test material is determined. This will indicate the concentration of the material even if at the final stage of the measurement the flat portion of the curve had shifted to the range of the used angle of incidence.

Figure 2:
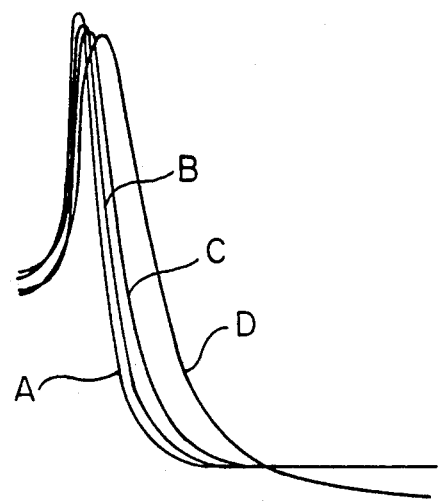
FIG. 2 illustrates the principle of the method in accordance with the invention.

FIG. 2 shows an experiment conducted with one of the materials of the invention, palladium. A 13.4 nm thick palladium layer was coated with monomolecular Cd-behenate layers in such a fashion that the number of the layers was increased from 2 to 8. A SPR-measurement was conducted after the addition of each pair of layers and the curves representing the intensity as a function of the angle of incidence were registered. The thickness of one Cd-behenate layer was 3 nm. In FIG. 2, a curve obtained with a bare palladium surface is denoted by letter A, the curve of two layers by letter B, the curve of four layers by letter C, and the curve of eight layers by letter D. It can be clearly seen in FIG. 2 that the changes taking place on the surface shift considerably the location of the down-way slope portion of the curve. Consequently, as the measurement is carried out at a suitable angle of incidence that is located within the downway slope portion in each of the curves obtained within the measurement range of the test material, the slope portions being well enough separated from each other, a maximum change of the intensity values and a good sensitivity is obtained as a result. FIG. 2 reveals that materials not used as SPR-materials because of certain prejudices can well be used also for this purpose if advantage is simultaneously taken of their catalytic properties.

Because palladium can be used as SPR-material it brings some new possibilities for SPR-analysis. The catalytic properties of palladium towards substances containing hydrogen make it very interesting considering the analysis of these substances. Palladium dissociates hydrogen on its surface and it has good affinity to some substances containing hydrogen. This feature has been utilized previously in semiconductor sensors measuring the concentrations of hydrogen-containing molecules. Substances that can be measured by means of palladium in these types of sensors are hydrogen sulphide, alcohols, ethylene etc. (J. Lundström, M. Armgarth, A. Spetz, F. Windquist, "Gas sensors based on catalytic metal-gate field-effect devices", Sensors and Actuators, 10, 399–421 (1986)).

Figure 3:
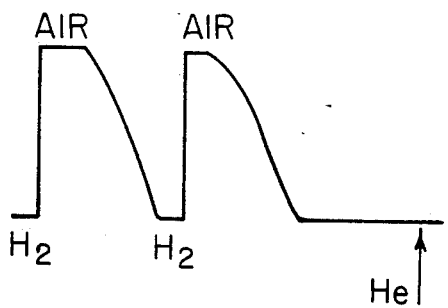
FIG. 3 shows a test carried out with a sensor in accordance with the invention.

FIG. 3 shows a SPR-test conducted with palladium. In the test hydrogen gas, air and helium were led to the surface of palladium in succession. The curve of FIG. 3 indicates the intensity value obtained by mean of the method of the invention as a function of time. As is apparent from the Figure, the sensitivity of palladium to hydrogen is clear and in addition the phenomenon is reversible. A special phenomenon is the rise of the intensity value caused by hydrogen. Because hydrogen has a smaller refractive index than air, the intensity values should decrease owing to the gaseous hydrogen led to the vicinity of the palladium surface. However, the intensity values raise considerably, which indicates the fact that hydrogen changes the properties of the surface layer of palladium itself owing to the catalytic properties of palladium. Moreover, only a minor pit caused by helium can be observed in the curve, which illustrates well the selectivity of palladium towards hydrogen.

Figure 4:
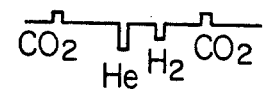
FIG. 4 shows a test carried out with a traditional sensor.

FIG. 4 shows in the scale of FIG. 3 the SPR-test conducted with gold, the conventional material. A considerable difference compared with palladium is that hydrogen causes the decrease of the intensity values, as expected. The results with other gases, carbon dioxide and helium, are also in conformity with the expectations.

Figure 5:
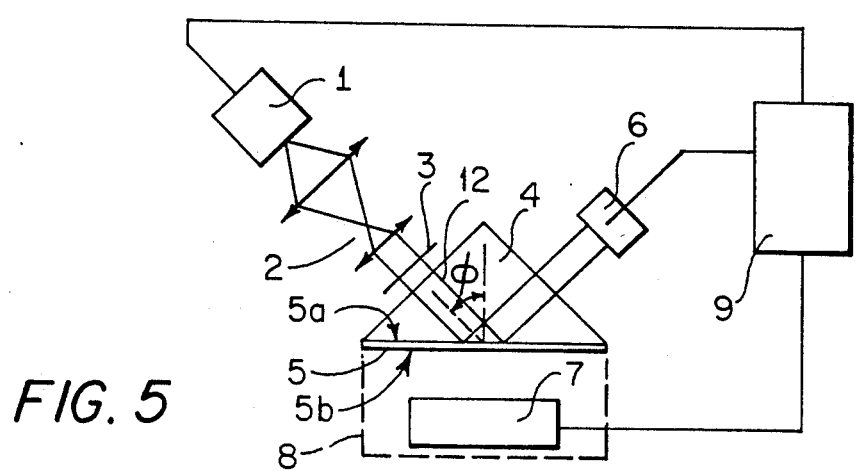
FIG. 5 shows a sensor in accordance with the invention and the auxiliary equipment associated therewith.

FIG. 5 shows a sensor that is particularly well suitable in the method according to the invention. The sensor comprises a monochromatic light source 1 and collimating optics 2 provided for making the light beam emanating from the light source 1 parallel and for directing it through a polarizer 3 to meet the surface 5a of the metal layer in a predetermined angle of incidence $\phi$. The metal surface is constituted of the inner surface of a metal film fixed on transparent dielectric material 4, a glass prism. The total reflection taking place on this surface leads the light beam to a detector 6. The light beam 1, the optics 2 and the prism 4 are so disposed that the collimated light beam strikes the interface 5 of the prism and the metal layer at an optimum angle of incidence $\phi$, which is within the measurement range of the test material in such a fashion that the steep portions of all the curves corresponding to the concentration values essential for a successful measurement are situated at the angle of incidence. In this way it is possible to obtain an intensity value or a time derivative of the intensity value that is proportional to the concentration.

On the other side 5b of the metal layer 5 is situated the material to be analyzed. In the case of palladium as the metal layer the material is some substance containing hydrogen. For example, a through flow cell can be used at this area and this area can be also isolated from the surroundings by means of a selective isolating layer 8, such as a membrane that passes only the substance to be analyzed through if the surroundings which are examined contain other substances towards which the material of the material layer shows catalytic properties. A radiation heater preventing the condensing of water molecules on the surface of the metal layer, known as such, is denoted by reference numeral 7 in the Figure.

An exact value for the angle of incidence $\phi$ can be calculated on the basis of several factors such as the thickness of the metal layer, the wavelength of light and the dielectric constants of the dielectric material 4 and metal 5 at this wavelength. For example, as palladium serves at the material of the metal layer 5 and He-Ne-laser serves as the light source at the wavelength 632,8 nm and with a prism of BK-7 optical glass, the thickness of the palladium layer should be 13 nm and the angle of incidence 42,7°.

The accuracy and selectivity can be improved by using also a so-called differential measurement having two light beams emanating from the same light source, one of them directed to an active part of the SPR-surface and the other of them to an inactive part of the same surface. The intensity difference of the reflected light beams is sued as the measurement data rather than the absolute intensity.

The so-called fixed-angle-method has been described hereinabove (only one angle of incidence), which can be realized with a sensitive and inexpensive sensor. However, the invention can also be applied in a method that utilized several angles of incidence simultaneously for a better measurement dynamics. The invention can also be applied for example in the sensor type disclosed in a previous patent application 901186 by the Applicant.

All the measurement data obtained in the above methods can be processed by means of a microprocessor 9 connected to the detector and being also capable of modulating the light sources and synchronizing the detector.

In all of the above cases sensor can be easily miniaturized by using available electro-optical components (LED:s, detectors, heaters) and fiber optical connections.

The method according to the invention makes it possible to use new sensor material and to analyze new substances by means of measurements based on the SPR-phenomenon. The invention can be applied in a very wide range, such as medical diagnosis, wood industry, process control, monitoring the condition of the environment, detecting leaks etc.

I claim:

1. A method for carrying out a surface plasmon resonance (SPR) measurement comprising:
    directing a beam of electromagnetic radiation through a part transparent to said radiation onto a surface of a material layer for reflection of said radiation therefrom, said material layer on its opposite surface being in contact with a test material; and
    measuring the change of intensity of the reflected radiation caused by the resonance phenomenon for analyzing the test material, wherein the material layers is a layer of a catalytic material having a negative real part of the dielectric constant at the used wavelength of the electromagnetic radiation of SPR-compatibility, and is capable of catalyzing a chemical reaction in which the test material takes part, the measurement being carried out at such a wavelength and angle of incidence of the radiation onto the surface that a change resulting from the contact of the test material with the opposite surface of said material of the material layer owing to the catalytic properties of the material is detectable in the intensity of the reflected radiation.

2. A method as claimed in claim 1, wherein said material layer consists of a metal catalyst.

3. A method as claimed in claim 2, wherein the material layer is selected from the group consisting of titanium, cobalt, nickel, platinum, aluminum, palladium and mixtures thereof.

4. A method as claimed in claim 3, wherein the material is palladium.

5. A method as claimed in claim 4, wherein the test material contains hydrogen.

6. A method as claimed in claim 5, wherein the test material is selected from the group consisting of hydrogen gas, ammonia, hydrogen sulphide, an alcohol and a hydrocarbon.

7. A sensor for carrying out a surface plasmon resonance (SPR) measurement, comprising:
    a source of electromagnetic radiation;
    a material layer having a surface exposed to electromagnetic radiation from said source and an opposite surface;
    means for bringing a test material in contact with the material on said opposite surface;
    means for directing the source of radiation relative to said surface of the material layer in such a fashion that the radiation meets said surface at an angle of incidence enabling a surface plasmon resonance phenomenon;
    a detector for measuring the intensity of the light beam which has been reflected from the surface of the material layer and has undergone said resonance; and
    a device for treating the intensity values, said material layer being catalytic material having a negative real part of the dielectric constant a the used wavelength of electromagnetic radiation of SPR-compatibility and being capable of catalyzing a chemical reaction in which the test material takes part.

8. A sensor as claimed in claim 7, wherein said material layer consists essentially of metal catalyst.

9. A sensor as claimed in claim 8, wherein the material of the material layer is selected from the group consisting of titanium, cobalt, nickel, platinum, aluminum, palladium and mixtures thereof.

10. A sensor as claimed in claim 9, wherein the material is palladium.

* * * * *